United States Patent [19]

Pitet et al.

[11] 4,167,566
[45] Sep. 11, 1979

[54] ANTITHROMBOTIC 2-PRENYL-3-OXO-5,6-DIARYL-AS-TRIAZENES

[75] Inventors: Guy Pitet, Toulouse; Henri Cousse, Castres; Gilbert Mouzin, Castres; André Delhon, Castres, all of France

[73] Assignee: Pierre Fabre, S.A., France

[21] Appl. No.: 884,733

[22] Filed: Mar. 9, 1978

[30] Foreign Application Priority Data

Mar. 9, 1977 [FR] France .................................. 77 07245

[51] Int. Cl.² .................... C07D 253/06; A61K 31/53
[52] U.S. Cl. ........................................ 42/249; 544/182
[58] Field of Search ......................... 544/182; 424/249

[56] References Cited

U.S. PATENT DOCUMENTS

| 3,510,483 | 5/1970 | Trepamier | 544/182 |
| 3,948,894 | 4/1976 | Lacefield | 424/249 |
| 3,979,516 | 9/1976 | Lacefield | 424/249 |
| 3,989,831 | 11/1976 | Lacefield | 424/249 |
| 4,018,923 | 4/1977 | Lacefield et al. | 424/249 |

*Primary Examiner*—Alan L. Rotman
*Assistant Examiner*—Natalie Harkaway
*Attorney, Agent, or Firm*—Gordon W. Hueschen

[57] ABSTRACT

The invention relates to compounds of the formula

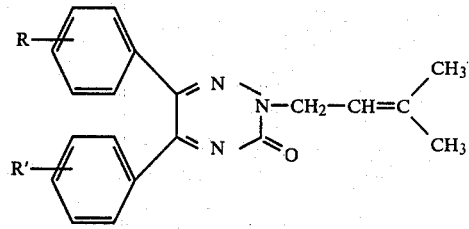

in which R and R' are identical or different and may be a hydrogen, an alkyl, a dialkylamino, an alkoxy, a halogen, or a hydroxy. These compounds are useful as drugs in the control of thromboses.

8 Claims, No Drawings

ANTITHROMBOTIC 2-PRENYL-3-OXO-5,6-DIARYL-AS-TRIAZENES

This invention, developed at the Pierre FABRE Research Center, concerns new chemical compounds, their process of manufacture, and their use in the control of thromboses.

These new compounds are 2-prenyl 3-oxo 5,6-diaryl as triazines of the general formula Formula I

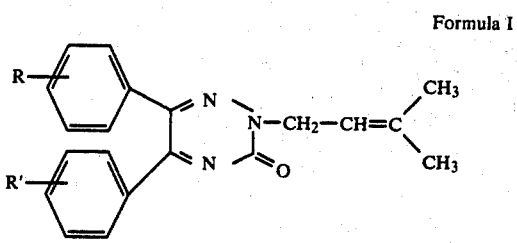

in which R and R' are identical or different and may be a hydrogen, a lower alkyl having 1 to 5 carbons, a dialkylamino, an alkoxy, a halogen, or a hydroxy.

They are located in ortho, meta or para position.

These compounds are obtained in accordance with the following reaction mechanism:

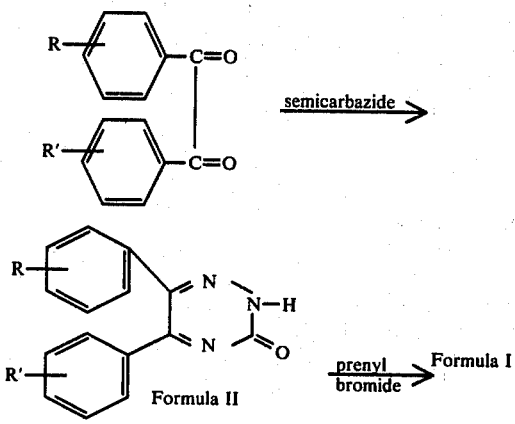

R and R' are as defined above.

The diketones, some of which are known, can be prepared in accordance with the following methods:

(a) dimerization of aldehydes in the presence of potassium cyanide

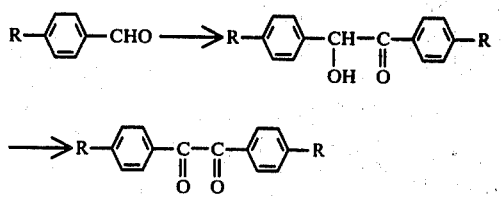

(b) the disymmetric α, α diketones are obtained:
either by rearrangement of a symmetric diketone with a differently substituted aldehyde in the presence of potassium cyanide, or
by dimerization in mixture of differently substituted aldehydes.

(c) Friedel and Craft's reaction between oxalyl chloride and an aromatic substrate, for instance

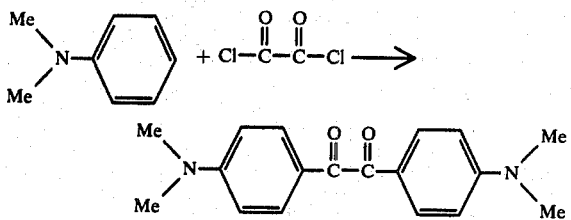

These symmetric or disymmetric diketones are treated with semicarbazide hydrochloride in acetic acid to obtain the triazines of formula II.

These triazines in methylene chloride are treated with prenyl bromide in the presence of 50% aqueous caustic soda.

By way of illustration and not of limitation we shall describe the preparation of a few compounds forming the object of the invention.

EXAMPLE 1

2-prenyl 3-oxo 5,6 di(paradimethylaminophenyl) as triazine (ST 804)

(a) Preparation of the intermediate triazine 890 g (3 mols) of p-dimethylamino benzil and 670 g of semicarbazide hydrochloride (6 mols) are added to a 10-liter reactor containing 3 liters of acetic acid. It is then heated for 2 hours at 115° C. The reaction mixture is cooled and poured into 12 liters of water with good agitation and then neutralized with about 2200 g of caustic soda, dissolved in 4 liters of water. The triazine precipitates in fine yellow crystals. The agitation is continued for 30 minutes and the suspension is then filtered. 1,000 g of triazine (quantitative yield) are recovered having the formula:

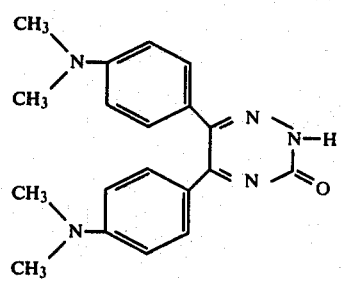

Yellow crystals
Melting point: 230° C.
Soluble in acids and dilute bases, poorly soluble in alcohol, benzene, methylene chloride, and chloroform. Insoluble in ether.

(b) PREPARATION OF ST 804

By the action of prenyl bromide in concentrated alkaline solution, the derivative substituted in 2-position is obtained by using the phase transfer technique by catalysis with a quaternary ammonium as described above.

2 liters of 50% caustic soda, 2 liters of methylene chloride, 3.5 g of benzyl triethyl ammonium chloride, and 334 g of intermediate triazine (1 mol) are added to a 10-liter reactor. 1.1 mol of prenyl bromide is then added.

The agitation is continued for 2 hours, whereupon the reaction mixture is poured into 8 liters of water with agitation and set aside for one hour. The organic phase is recovered and washed with water until neutral.

After drying over sodium sulfate, the organic phase is concentrated, whereupon, by precipitation by the addition of hexane, ST 804 is obtained in a yield of 85%, having the formula

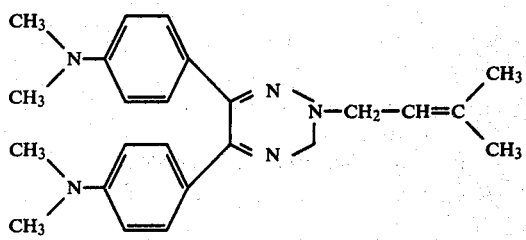

Orange yellow crystals.
Melting point: 210° C.
Soluble in dilute acids, methylene choride and alcohol. Insoluble in water, dilute bases, and ether.

EXAMPLE 2

Preparation of 2-prenyl 3-oxo 5,6-di(paramethoxyphenyl) as triazine (ST 793)

By proceeding in the same manner as above but using as intermediate the triazine of the formula

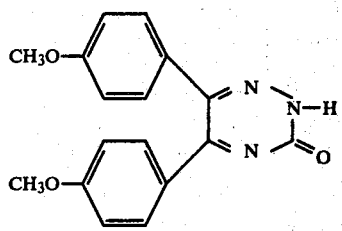

ST 793 of the formula

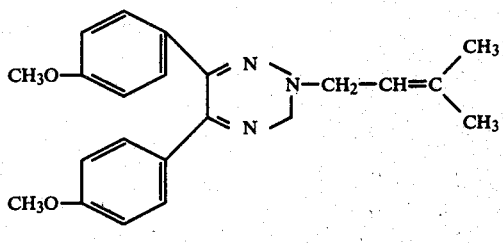

is obtained in a yield of 90%.
Yellow crystals
Melting point: 103° C.
Insoluble in water, dilute bases and acids, and ether.
Soluble in alcohol, benzene, and chloroform.

EXAMPLE 3

2-prenyl 3-oxo 5,6-di(parahydroxyphenyl) as triazine (ST 853)

By splitting off the methoxy of ST 793 with 48% hydrobromic acid ST 853 of the formula

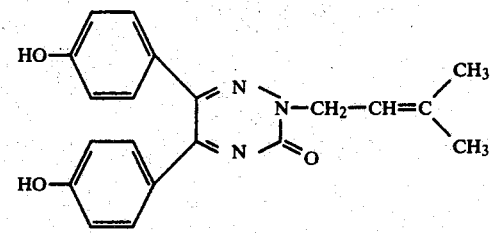

is obtained in a yield of 75%.
Yellow crystals
Melting point: 155° C.
Insoluble in water and ether.
Soluble in dilute bases and acids, methylene chloride, and alcohol.

EXAMPLE 4

2-prenyl 3-oxo 5(orthochlorophenyl) 6(p-dimethyl amino phenyl) as triazine

By operating as in Example 1, but using the intermediary triazine of the formula:

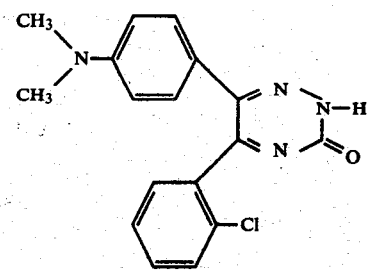

the product of formula

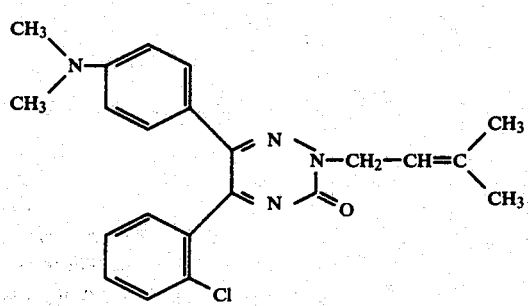

is obtained in a yield of 70%.
Orangish-yellow crystals
Melting point 160° C.
Soluble in dilute acids, methylene chloride and alcohol.
Insoluble in water, dilute bases, and ether.

PHARMACOLOGICAL STUDY

The following products were subjected to pharmacological screening. By way of example, we indicate the properties of a few compounds of this series.

(A) TOXICITY

According to C. MILLER and M. L. TAINTER—Proc. Soc. Biol. Med., 1944, 57, 261

| Products | LD$_{50}$ mg/kg mice, orally |
|---|---|
| ST793 | <1000 |
| ST804 | <1000 |
| ST853 | 800 |

(B) Antiaggregant Properties

The antiaggregant activity of the products ST 793 and ST 804 had been researched in vitro and ex vivo by the photometric technique of BORN G. V. R., ROSS J. - J. Physiol., 168, 178, 1962.

(a) In Vitro Study

The products were dissolved in polyethylene glycol 300. The antiaggregant activity was determined by adding 10 microliters of PEG 300 alone (control), or 10 microliters of product dissolved in PEG 300, to 300 microliters of plasma rich in rabbit platelets, to which there had been added 90 microliters of Michaelis Buffer pH 7.35 about one minute before the addition of sodium arachidonate (SIGMA product, Item A 1391).

The final molar concentration of aggregant agent used is equal to $2 \times 10^{-4}$ M.

Results expressed in final molarity mols/ml.

ST 793 total inhibition zone with $1.5$-$10^{-6}$
ST 804 total inhibition zone with $3$-$10^{-6}$
Aspirin (control product) total inhibition zone with ($10^{-3}$ M).

(b) EX Vivo Study

The products were administered orally for four consecutive days to albino guinea pigs, the treatment on the fourth day being carried out about 2 hours before the taking of blood.

Moreover, a first blood sample was also taken before the start of the treatment, each animal being thus its own control.

A group of animals receiving only the vehicle by itself was studied under strictly analogous conditions and constitutes the vehicle control lot.

The aggregation of the blood platelets was effected by adding collagen and arachidonic acid in vitro to the platelet-rich plasmas coming from the experimental animals.

Results

ST 793:
Doses studied: 5-10-20 mg/kg/day
total inhibition of aggregation by arachidonic acid as from 5 mg/kg.
More than 50% inhibition of aggregation by collagen with 10 and 20 mg/kg/day, tending to be total the higher the dose.

ST 804:
Dose studied 20 mg/kg/day.
Almost total inhibition of aggregation by both agents.

Aspirin:
Doses studied: 5-10-25 mg/kg/day.
5-10 mg/kg: total inhibition of aggregation by arachidonic acid.
25 mg/kg: total inhibition of aggregation by arachidonic acid, inhibition of aggregation by collagen.

(c) Antithrombotic activity
Thromboembolism with arachidonic acid in mice.
Reference: Intravenous arachidonate in the mouse.
A model for the evaluation of antithrombotic drugs.
KOHLER—WOODING—ELLENBOGEN
Thrombosis Research vol. 9, pages 67-80 (1976).

Principle

The intravenous administration of sodium arachidonate in the mouse causes respiratory distress followed in high dose (100 mg/kg), by the death of the animal. It was possible to correlate this respiratory distress with histological evidence of platelet aggregation in the microcirculation of the lungs. Drugs which inhibit aggregation with collagen and with prostaglandin synthetase are capable of blocking the effects of the arachidonate in vivo.

Results (a) Action with respect to the intravenous administration of a high dose of sodium arachidonate (100 mg/kg).

Administration of the products orally for four consecutive days in a dose of 100 mg/kg/day, last administration 2 hours before the intravenous injection of sodium arachidonate.

Controls: 9 dead out of 10; 1 mouse, recovery at +1440 seconds.
ST 793: 1 dead out of 10; 3 mice, recovery at > +1800 seconds; 6 mice: average time of recovery +477 seconds.
ST 804: 1 dead out of 10; 2 mice, recovery at > +1800 seconds; 7 mice: average time of recovery +249 seconds.

(b) Action in low dose with respect to the intravenous administration of 80 mg/kg of sodium arachidonate.

Administration of the products orally for five consecutive days in low dose (3 mg/kg/day). Last administration two hours before the intravenous injection of sodium arachidonate.

Controls: 7 dead out of 10; 1 mouse, recovery at +1800 seconds; 2 mice: average time of recovery: +1225 seconds
Aspirin: 9 dead out of 10; 1 mouse: recovery at +520 seconds
ST 793: 2 dead out of 10; 1 mouse: recovery at > +1800 seconds; 7 mice: average recovery time +373 seconds
ST 804: 2 dead out of 10; 1 mouse recovery at > 1800 seconds; 7 mice: average recovery time: +774 seconds.

Therapeutic Applications

In view of their pharmacological properties these products are useful for controlling thromboses.

What we claim is:

1. A compound of the formula

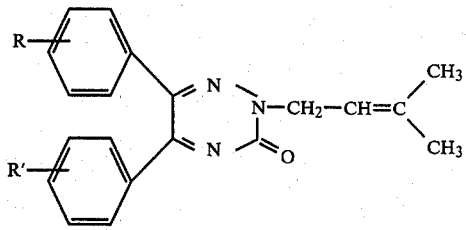

in which R and R' are identical or different and are selected from the group consisting of lower alkyl having 1 to 5 carbon atoms, dialkyl amino, alkoxy, halogen, and hydroxy.

2. A compound according to claim 1, selected from the group consisting of
- 2-prenyl-3-oxo-5,6-di(paradimethylaminophenyl)-as-triazine,
- 2-prenyl-3-oxo-5,6-di(paramethoxyphenyl)-as-triazine, and
- 2-prenyl-3-oxo-5,6-di(parahydroxyphenyl)-as-triazine.

3. A compound of claim 1 which is 2-prenyl-3-oxo-5,6-di(paradimethylaminophenyl)-as-triazine.

4. A compound of claim 1 which is 2-prenyl-3-oxo-5,6-di(paramethoxyphenyl)-as-triazine.

5. A compound of claim 1 which is 2-prenyl-3-oxo-5,6-di(parahydroxyphenyl)-as-triazine.

6. A method for the control of thrombosis in a patient subject thereto, comprising the step of administering to the said patient a compound of claim 1 in an antithrombotic amount.

7. The method of claim 6 wherein the compound is a compound of claim 2.

8. The method of claim 6 wherein the compound is administered in an amount of at least about three milligrams per kilogram per day.

* * * * *

UNITED STATES PATENT AND TRADEMARK OFFICE
CERTIFICATE OF CORRECTION

PATENT NO. : 4,167,566
DATED : September 11, 1979
INVENTOR(S) : Pitet et al.

It is certified that error appears in the above-identified patent and that said Letters Patent are hereby corrected as shown below:

[54] Title; "TRIAZENES" should read -- TRIAZINES --

Col. 3, last formula;

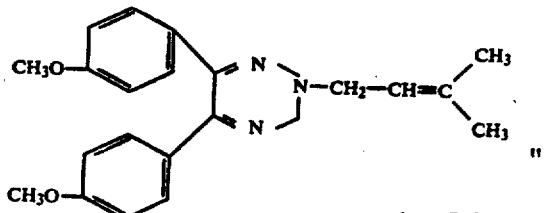 should read -- 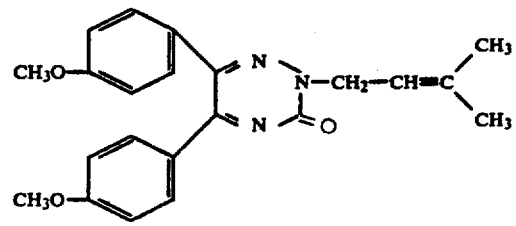 --

Col. 3, line 24; "choride" should read -- chloride --
Col. 3, first formula

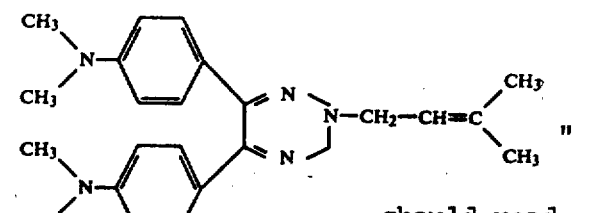 should read -- 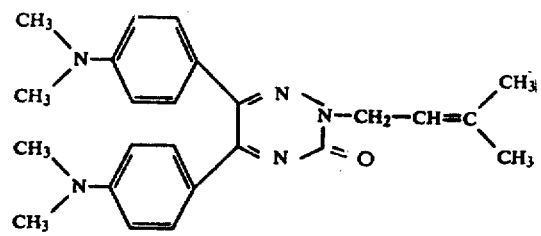 --

UNITED STATES PATENT AND TRADEMARK OFFICE
CERTIFICATE OF CORRECTION

PATENT NO. : 4,167,566

DATED : September 11, 1979

INVENTOR(S) : Pitet et al.

It is certified that error appears in the above-identified patent and that said Letters Patent are hereby corrected as shown below:

Col. 5, second column in table, lines 2 & 3 (both lines); "<1000" should read -- >1000 --

Col. 5, line 65; "(c) Antithrombotic activity" should be centered as a heading like (a) and (b).

Signed and Sealed this

Fourth Day of December 1979

[SEAL]

Attest:

SIDNEY A. DIAMOND

Attesting Officer    Commissioner of Patents and Trademarks